(12) United States Patent
Cavanaugh et al.

(10) Patent No.: US 9,137,991 B1
(45) Date of Patent: Sep. 22, 2015

(54) CHOLINE CONTAINING COMPOSITION AND METHOD OF USE

(71) Applicants: Kevin Cavanaugh, Collierville, TN (US); Timothy B Cartwright, Germantown, TN (US)

(72) Inventors: Kevin Cavanaugh, Collierville, TN (US); Timothy B Cartwright, Germantown, TN (US)

(73) Assignee: Floratine Products Group, Inc., Collierville, TN (US)

( * ) Notice: Subject to any disclaimer, the term of this patent is extended or adjusted under 35 U.S.C. 154(b) by 185 days.

(21) Appl. No.: 13/675,423

(22) Filed: Nov. 13, 2012

Related U.S. Application Data

(60) Provisional application No. 61/590,972, filed on Jan. 26, 2012.

(51) Int. Cl.
*A01N 33/12* (2006.01)
(52) U.S. Cl.
CPC ...................................... *A01N 33/12* (2013.01)
(58) Field of Classification Search
CPC ...................................................... A01N 33/12
USPC ............................................................ 504/345
See application file for complete search history.

(56) References Cited

U.S. PATENT DOCUMENTS

| | | | |
|---|---|---|---|
| 4,443,242 A | | 4/1984 | Fox |
| 5,116,605 A | * | 5/1992 | Alt .................................. 514/78 |
| 5,123,950 A | * | 6/1992 | Homma et al. ................... 71/11 |
| 5,124,061 A | | 6/1992 | Geary, Sr. |
| 5,287,826 A | | 2/1994 | Mohamed |
| 5,321,040 A | | 6/1994 | Huang et al. |
| 5,355,837 A | | 10/1994 | Reyes |
| 6,207,615 B1 | | 3/2001 | Miller |
| 6,436,165 B1 | | 8/2002 | Konzak et al. |
| 6,451,741 B1 | | 9/2002 | Watschke |
| 6,455,468 B1 | * | 9/2002 | Li et al. ......................... 504/125 |
| 6,642,179 B2 | | 11/2003 | Watschke |
| 7,030,060 B1 | * | 4/2006 | McDonald et al. ........ 504/116.1 |
| 7,494,526 B2 | | 2/2009 | Yavitz |
| 2005/0119127 A1 | * | 6/2005 | Cambri et al. ................. 504/172 |
| 2005/0208191 A1 | * | 9/2005 | Saimanohar et al. ......... 426/549 |
| 2007/0036831 A1 | * | 2/2007 | Baker ........................... 424/400 |
| 2012/0103041 A1 | * | 5/2012 | Smith et al. ....................... 71/27 |
| 2014/0194289 A1 | * | 7/2014 | Sclapari et al. ............... 504/206 |

FOREIGN PATENT DOCUMENTS

WO        WO 0063138 A1 * 10/2000

OTHER PUBLICATIONS

The Pharmaceutics and Compounding Laboratory, Eschelman School of Pharmacy, University of North Carolina; Emulsions: Preparations and Stabilization, Natural Emulsifying Agents [Retrieved from internet <URL: http://pharmlabs.unc.edu/labs/emulsions/natural.htm >] [Downloaded Jul. 11, 2014], excerpt in action.*

(Continued)

*Primary Examiner* — Anna Pagonakis
*Assistant Examiner* — Miriam Levin
(74) *Attorney, Agent, or Firm* — Harris, Shelton, Hanover & Wash; Susan B Fentress

(57) ABSTRACT

This invention pertains to a choline containing composition, delivered through a delivery system, to reverse the negative effects of urine on plants, containing turf grass, ornamental flowers, shrubs and bushes. The invention also provides method to deliver choline containing products to the foliar portion of plants.

16 Claims, 3 Drawing Sheets

(56) References Cited

OTHER PUBLICATIONS

Dong Ahn, Egg Components, (Animal Science Department, Iowa State University), [Retrieved from internet <URL: http://www.public.iastate.edu/~duahn/teaching/Neobiomaterials%20and%20Bioregulation/Egg%20Components.pdf >] [Downloaded Jul. 11, 2014], document is 67 pages; 7 selected pages attached: cover (p. 1), 2, 5, 6, 17, 19, 20).*

The Merck Index Online, Choline, [Retrieved from internet <URL: https://www.rsc.org/Merck-Index/monograph/print/mono1500002211/choline?q=authorize>] [Downloaded Jul. 11, 2014], 2 pages.*

Jena Bioscience, L-α-Phosphatidylcholine, chicken egg, sodium salt; [Downloaded from internet <URL: http://www.jenabioscience.com/images/5103fef174/LI-004.pdf >] [Downloaded Jul. 11, 2014], 1 page.*

The American Egg Board, Egg Products Reference Guide (2006), [Retrieved from internet <URL: http://www.aeb.org/images/website/documents/food-manufacturers/order-aeb-resources/Egg_Products_Reference_Guide.pdf >], 8 pages.*

Friedman et al., The Emulsifying Properties of Gelatin Systems, J. Am. Chem. Soc. (1931) 53 (8): 2898-2901,4 pages.*

* cited by examiner

Control (No Applications)

CHOLINE CONTAINING COMPOSITION AND METHOD OF USE

CROSS REFERENCED TO RELATED APPLICATIONS

This application claims the benefit of U.S. Application Ser. No. 61/590,972 filed Jan. 26, 2012 under 25 U.S.C. §119 (e) hereby specifically incorporated by reference in its entirety.

FIELD OF INVENTION

This invention relates to a choline containing composition and a method to use this composition to mitigate damage caused by animal urine to plants.

BACKGROUND OF THE INVENTION

Plants put up many barriers to the retention, entry and transport of active agents, such as growth inhibitors and stimulators. In addition, environmental conditions and plant factors (age, architecture, leaf morphology and leaf arrangement) may decrease the activity of a plant modulator. Adjuvants are commonly used to improve the performance of plant modulator performance.

Foliar feeding wasn't commercially successful until the 1960's when a few farmers increased yields in selected crops and improved the activity of herbicides. Foliar feeding methods are known in the art. U.S. Pat. No. 7,494,526 discusses the use of nanoscalor encapsulation of nutrition that can be absorbed foliarly. U.S. Pat. No. 4,443,242 discloses the use of an aerosol propellant to apply oil-based emulsions onto plant tissue. U.S. Pat. No. 6,436,165 disclosed the use of a soy lecithin to act as a spreader-sticker to enhance foliar uptake of all fertilizer combinations and increase the shelf-life of the product. U.S. Pat. Nos. 5,321,040, 6,451,741 and 6,642,179 describe the use of foliarly applied foam as the delivery system for pesticides, fungicides or plant growth regulators.

More recently, the most extensive and effective use of foliar feeding lies within the turf industry, namely golf courses and sports fields. In these industries, the primary method of delivery of nutrients to the leaf surface is by spraying a fine mist made of a dilute solution of nutrients and quite frequently with an adjuvant. However, this method has drawbacks of being labor intensive, subject to inaccurate measurements of the nutritional compounds, subject to improper sprayer operation and interference by natural factors, such as wind and rain.

The use of foliar feeding on plants in horticulture or landscaping is unknown. These plants are primarily fed by soil applied granular applications or through "hose-end" applicators containing water soluble nutrients applied to the soil.

There are many patents pertaining to the mitigation of urine damage on turf. U.S. Pat. No. 6,207,615 discusses the use of nitrogen, phosphorus and potash fertilizer combined with granular gypsum to enhance the growth of the turf surrounding the spot. U.S. Pat. No. 5,355,837 claims that the use of absorbent pads in a specially designed toilet station will prevent damage by directing the canine to the pads. U.S. Pat. No. 5,287,826 describes a chemical that, when applied to only one spot, will entice the pet to preferentially use that spot and not any other location in the yard. It would be advantages to develop at composition and method to mitigate damage caused to plants by pet urine.

SUMMARY OF THE INVENTION

This invention provides a composition made of an active agent solubilized in a surfactant, wherein the active agent includes choline. More specially, the present invention relates to the controlled delivery of a choline containing composition to plants, containing but not limited to: turf grass, ornamental flowers and shrubs and bushes. In the preferred embodiment, the choline containing composition is used to mitigate the damage caused by animal urine.

Additionally this invention provides a foam composition made of an active agent: including choline made by the process including the steps of solubilizing a sufficient amount of an active agent including choline in a nonionic surfactant in a container under pressure, dispensing the solubilized active agent from the container, wherein the nonionic surfactant forms a foam as it is discharged from the container.

This invention further relates to a method for treating urine damage in plants by contacting foliar portions of the plants with the foam composition of this invention. There is further provided a method for mitigating urine damage to plants by applying choline containing fertilizer or nutritional supplement.

BRIEF DESCRIPTION OF THE SEVERAL VIEWS OF THE DRAWING

For a fuller understanding of the nature and desired objects of the present invention, reference is made to the following detailed description taken in conjunction with the accompanying drawing figures.

DETAILED DESCRIPTION OF THE INVENTION

Figure 1:
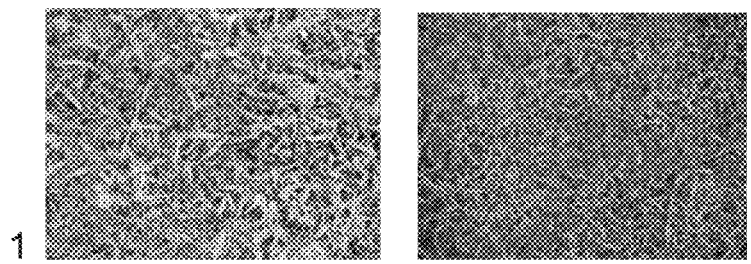
FIG. 1 shows that Plot 1 is the control of the experiment of the present invention.

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification containing the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

This invention pertains to the use of choline containing composition and method to mitigate damage caused by animal urine to plants. The infusion of choline into the plant through foliar absorption or root uptake can offset the negative effects of excess trimethylamine, nitrogen and salt that has entered the turf through pet urination. Therefore, it is desirable to develop a choline containing composition and a method to administrate the composition to negate urine damage on plants. The mode-of-action to counter the effects of urine include but are not limited to: prevention of the methylization of DNA; enhance the production of betaine, which improves cell membrane integrity, which enhances salt tolerance, and reduction of excess nitrogen through the improved production of mature proteins.

In the present invention, the primary active agent is a choline. Choline has the composition: N-hydroxyethyl-N, N, N-trimethyl ammonium hydroxide. The term choline means a salt of choline or its metabolites including: betaine, acetylcholine, and/or phosphatidyl choline. The choline containing composition can include an effective amount of four choline derivatives: choline, betaine, acetycholine, and phosphatidyl choline. In one embodiment, the choline containing composition includes choline bitartrate. The choline is added to the canine urine treatment composition at a rate of between 1% to 5% by weight. Additionally, the composition can include other agents that have the physical property of reducing or rectifying plant damage from a canine urine deposition or that do not interfere with the activity of the active agent, but have other activity useful to plants.

In the present invention, compounds having vitamin K activity can be included in the canine urine treatment composition. Vitamin K is a group of structurally similar, fat soluble vitamins that are needed for the posttranslational modification of certain proteins required for blood coagulation and in metabolic pathways in bone and other tissue. They are 2-methyl-1,4-naphthoquinone (3-) derivatives. This group of vitamins includes two natural vitamins: vitamin $K_1$ and vitamin $K_2$. The salts of vitamin K are preferably sodium or potassium salts. Both forms of vitamin K were most effective at an addition rate between 0.1% to 0.5% by weight.

Additionally, compounds having vitamin B activity can be included in the canine urine treatment composition. Compounds having vitamin B activity include a group of water-soluble vitamins including thiamine, riboflavin, niacin, pantothenic acid, biotin, pyridoxine, folic acid, inositol, and vitamin $B_{12}$. In one embodiment, salts of vitamin $B_9$ and vitamin $B_{12}$ are included in the active ingredients of the choline containing composition. Vitamin $B_9$ and Vitamin $B_{12}$ were added to the composition at equivalent amounts between 0.1% to 0.5% by weight.

The choline containing composition can also include elemental nutrition, such as but not limited to, nitrogen, phosphorus, potassium, calcium, magnesium, silicon, sulfur, iron, zinc. Bio-stimulant nutrition includes, but is not limited to, hormones, vitamins, amino acids, enzymes, organic acids such as humic or fulvic acid, sugars, catalysts, water and antioxidants. Other non-active ingredients such as wetting agents and fillers can be included in the choline containing composition The choline containing composition can be can applied with humic or fulvic acids. The humic or fulvic acid portion should not exceed 0.5% by weight of the composition.

The application of this product was carried out in three primary forms: 1) a dilute spray (1-3% by volume) misted onto the test plots followed by heavy watering; 2) sprayed onto the foliage using a foam carrier; and 3) poured in a more concentrate solution (5-10% by volume) on to the affected areas and then watered-ion. All three forms of application showed positive results, but the procedure described in 2) above was most effective.

The present invention also relates to a method to incorporate the choline containing composition into a pressurized foam application system. The composition can also be delivered through a foam delivery system, to reverse the negative effects of urine on plants, containing turf grass, ornamental flowers, shrubs and bushes. The invention also provides method to deliver choline containing composition to the foliar portion of plants. The choline containing compositions are delivered to the foliar portion of the plants by the process of: solubilizing a sufficient amount of an active agent in a non-ionic surfactant in a container under pressure, dispensing the solubilized active agent from the container, wherein the non-ionic surfactant forms a foam as it is discharged from the container and contacting foliar portions of the plants with the foam.

It is the art of this invention that allows the larger molecules, such as humic acids, sugars, vitamins, biostimulants and extracts to be easily absorbed and translocated throughout the plant. By contrast, the soil application of these compounds is quite inefficient due to interference from soil physicality, incompatible soil chemistry and microbiological decimation. It is the unique nature of this application that allows these key molecules to by-pass the various barriers and be properly utilized within the plant.

In one embodiment of the invention, the choline containing composition is a blend of four choline derivatives: choline, betaine, acetylcholine, and phosphatidyl choline. An important part of this invention is the successful solubilization and blending of the effective amount of these compounds. The present invention also relates to a method to incorporate the choline containing composition into a pressurized foam application system.

Surfactants are compounds that lower the surface tension of a liquid, the interfacial tension between two liquids, or that between a liquid and a solid. Surfactants may act as detergents, wetting agents, emulsifiers, foaming agents, and dispersants. In the instance of the foam cans, the non-ionic surfactant is used primarily as the foaming agent. Nonionic surfactant are not dependent on a surface-active anion for effect. They include many long chain alcohols such as polyethylene glycol. Other prominent examples are fatty alcohols including cetyl alcohol, stearyl alcohol, and cetostearyl alcohol (consisting predominantly of cetyl and stearyl alcohols), and oleyl alcohol and phosphatidylethanolamine.

In one embodiment, proper use of the product involves spraying the choline based, pressurized foam product directly to the affected area. Urine neutralization will occur whether or not the site is watered. Best results are achieved when the product is applied as soon as possible after urination and watered-in.

Foam disperses the active agent to the foliar portion of plants. The foam is delivered by an aerosol propellant through a nozzle and onto the above-ground parts of plants. The nutritional foam can be sprayed on a wide variety of plants but is intended to be used on horticultural species typically found in greenhouses, nurseries, homes and landscaping. The nutritional portion of the foam can be designed and tailored to fit any agronomic need.

The "aerosol can" delivery system insures a constant and uniform application of foam and nutrition to cover the equivalent area of 180 square feet. The foam acts as a sight guide to the user to prevent overdosing or leaving untreated areas. The foam is made of a surfactant that is non-phytotoxic and collapses in just a few seconds after spraying to uniformly distribute the nutrients over the plant surfaces. The non-ionic nature of the surfactant prevents the unnecessary tie-up with micronutrients and can solubilize a wide variety of active agents.

Testing of the nutritional foam has successfully increased root mass, rapid topical growth, improved color and increased flowering. The trial results showed an increase in stem growth, leave size, root mass and flowering. In some instances the stem length increased by 400% while the number of flowers per stem increased 300%. The procedure consisted of the weekly application of the foam product on all above ground parts of the plants.

The urine damage treatment composition of the present invention include a combination of several components. It has been discovered that a mixture of the components described herein is more effective on mitigating urine damage on plants than are the individual components.

Canine Urine Study

In another preferred embodiment, an experiment was designed to study the effects of mitigation product on canine urine damaged turf-grass. Eight Plots of common Bermudagrass were subdivided and a study was conducted to discover if the use of urine mitigation product(s) would increase the rate of grass growth and recovery from the damages of urine applications. The study utilized collected canine urine (both male and female) from greyhounds.

All plots were pre-treated with a general purpose granular lawn fertilizer of 13-13-13 prior to the study. Weekly foliar applications were applied to all plots consisting of FPG foliar products: ASTRON, PROTESYN and 4-4-16 (Floratine Products Group, Inc. Collierville, Tenn.). ASTRON (Floratine Products Group, Inc. Collierville, Tenn.) provides hormones, vitamins, macro and micro nutrients and root stimulating biostimulant. PROTESYN (Floratine Products Group, Inc. Collierville, Tenn.) provides all L-amino acids, carbohydrates and simple proteins with a 6-2-3 analysis. Foliar 4-4-16 (Floratine Products Group, Inc. Collierville, Tenn.) is a nutritional supplement providing 4% Nitrogen, 4% Phosphorous, and 16% Potassium.

All plots were irrigated daily to increase grass growth. After one week, the plots were treated with 3 ounces of canine urine and sprayed with compositions 1 and 2, fertilizer daily and/or weekly as outlined on the plot map below.

Compositions 1 and 2 fertilizer daily and/or weekly as outlined on the Table 1 plot map below.

Composition 1 contains choline to offset negative effects of from urine. In addition to choline (choline bitartrate), composition 1 contains vitamin K, choline, an emulsifier such as monoethanolamine MEA, folic acid in a KOH solution, Trimethylglycine TMG, Thiamine B-12, sugar in water. The optimum percentages of these compounds are TMG (1-10% by weight), folic acid dissolved in a KOH solution (0.1-0.5% by weight), MEA (1-10% by weight) and sugar (5-10% by weight). Composition 1 is administered through the foam delivery system to the affected turf for the urine mitigation at a concentration within the pressurized can of between 4 and 8%.

Composition 2 is essentially Composition 1 enhanced with humic acid, iron (Fe) and/or zinc (Zn), along with a penetrating wetting agent for increasing water moment through the soil. The concentration of iron should be between 0.5 and 1.0% by weight and the zinc portion should be between 0.1 and 0.5% by weight. The quantity of penetrating wetting agent in Composition 2 should be no more than 1.0% by weight. The "penetrating" wetting agent is anionic in nature. The negative charge on the wetting agent molecule repels the negative charge on the soil colloids and temporarily increases the size of the capillary space within the soil matrix. In the case of the foam cans, this anionic wetting agent is used in addition to the non-ionic surfactant used for foaming.

All pictures were taken of plots daily to compare and monitor the changes in the plots after each application over time.

FIG. 1 shows that Plot 1 is the control of the experiment. No urine was used to treat Plot 1.

As illustrated in TABLE 1, all plots were treated with 13-13-13 fertilizer. A foliar treatment was applied weekly to all plots. Plots received irrigation daily.

Figure 2:
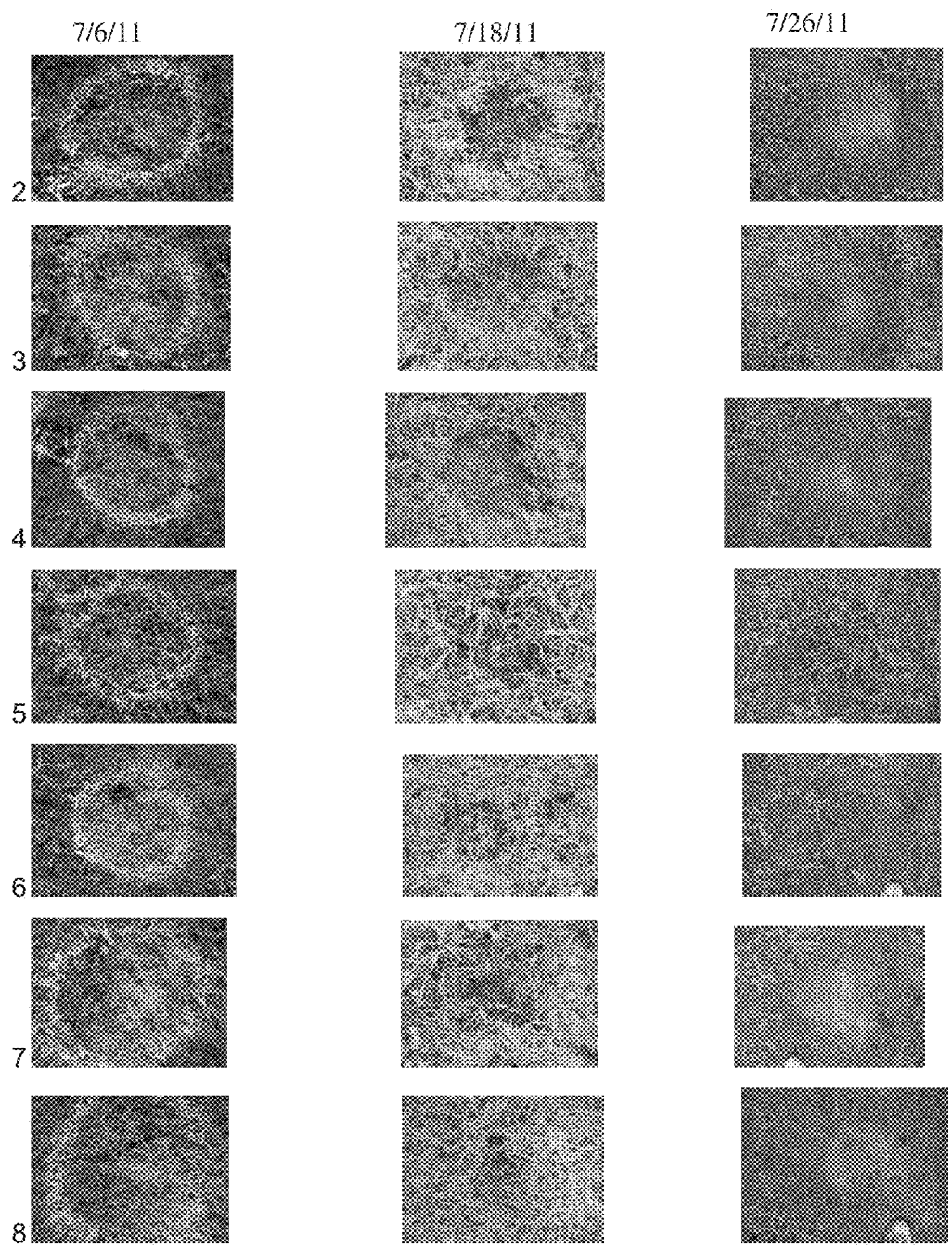
FIG. 2 shows Plots 2 to 8 which compared the effect of compositions 1 and 2 and combination of compositions 1 and 2 on turf grass after urine applications.

Now referring to FIG. 2, all plots were initially treated with urine daily. After two weeks of daily urine application, compositions 1 and 2 were applied daily or weekly. As illustrated in TABLE 2, Plot 2 was treated with urine daily only. Plots 3, 4, 5, and 6 were treated with urine daily until 7/18. Urine applications on plots 3, 4, 5, and 6 were stopped on day 29, but foliar and fertilizer application continued. Starting from day 15, Plot 3 was treated with composition 1 daily, Plot 4 was treated with composition 2 daily, Plot 5 was treated with composition 1 daily and composition 2 daily, and Plot 6 was treated with composition 1 weekly.

As illustrated in FIG. 2, on day 29, after 13 days of composition 1 and/or 2 composition treatments, Plots 5 and 6 showed the most improvement, but did not completely recover from the urine applications. Plots 5 and 6 completely recovered after two weeks with composition 1 weekly only (Plot 6), and composition 2 daily, plus composition 1 with daily applications (Plot 5). Plots 7 and 8 showed improvement after composition 2 was applied with daily & weekly treatments. Plots 7 and 8 completely recovered in another two weeks, after the application of urine when composition 1 was applied with daily and weekly applications.

Figure 3:
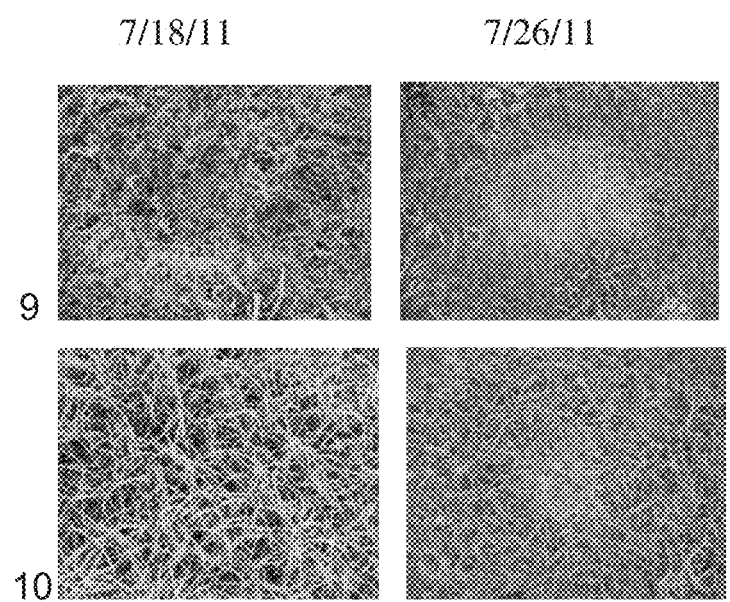
FIG. 3 shows Plots 9 and 10 which compared the effect of compositions 1 and 2 on turf grass after urine applications.

Now referring to FIG. 3 and Table 1, on day 16, Plots 9 and 10 were added. Plots 9 and 10 were treated with canine urine before the application of fertilizer. These plots were treated with urine only for 1½ weeks. Then Plot 9 was treated with urine, compositions 1 and 2 as a 50% solution daily, and Plot 10 was treated with Urine Compositions 1 and 2 daily as two separate applications. Both Plots 9 and 10 showed little improvement with the daily application of urine plus fertilizers. Plots 13, 14, 15, and 16 were added on day 51. Plots 13, 14, 15, and 16 were treated with urine daily and composition 1 daily or weekly. The plots had little recovery during the application of urine. Plots 13, 14, 15, 16 showed less damage with the application of Composition 1 weekly when compared with application of composition 1 daily.

TABLE 1

Plots Application Summary

Plot No.
Day 1 13-13-13
Day 2 Irrigate, Foliar
Day 3 Irrigate
Day 4 Irrigate
Day 7 Irrigate
Day 8 Rain
Day 9 Irrigate, 2, 3, 4, 5, 6, 7, 8
Day 10 Irrigate, 2, 3, 4, 5, 6U, 7U, 8U
Day 15 Irrigate, Foliar, 2, 3, 4, 5, 6, 7, 8
Day 16 Irrigate, 2, 3, 4, 5, 6U, 7U, 8U,9U, 10U
Day 17 Irrigate, 2, 3, 4, 5, 6U, 7U, 8U,9U, 10U
Day 18 Rain, 2, 3, 4, 5, 6U, 7U, 8U,9U, 10U
Day 19 Irrigate, Foliar, 2, 3, 4, 5, 6, 7, 8, 9U, 10 U
Day 22 Irrigate, 2, 3, 4, 5, 6, 7, 8, 9U, 10 U
Day 23 Irrigate, 2, 3, 4, 5, 6, 7, 8, 9U, 10 U
Day 24 Irrigate, 2, 3, 4, 5, 6, 7, 8, 9U, 10 U
Day 28 Irrigate, Foliar, 2, 7, 8, 9, 10 ( 3, 4, 5, 6, No Urine)
Day 29 Irrigate, Mowed, 2, 7, 8, 9, 10 ( 3, 4, 5, 6, No Urine)
Day 30 Irrigate, 2, 7, 8, 9, 10 ( 3, 4, 5, 6, No Urine)
Day 31 Irrigate, 7, 8, 9, 10 ( 3, 4, 5, 6, No Urine)
Day 32 Irrigate, 7, 8, 9, 10 ( 3, 4, 5, 6, No Urine)
Day 41 Irrigate, Foliar 7,8,9, 10
Day 42 Irrigate, 7,8,9, 10
Day 43 Irrigate, 7,8,9, 10
Day 44 Irrigate, 7,8,9, 10
Day 45 Irrigate, 7,8,9, 10
Day 46 Irrigate, Foliar, 7,8,9, 10

TABLE 1-continued

Plots Application Summary

Day 47 Irrigate, 7,8,9, 10
Day 48 Irrigate, 7,8,9, 10
Day 49 Irrigate, Foliar, 7,8,9, 10,11,12
Day 51 Irrigate 13,14,15,16 (7,8 Composition 1 daily, No Urine
Day 52 Irrigate 13,14,15,16 (7,8 Composition 1 daily, No Urine
Day 56 Irrigate, Foliar 13,14,15,16
Day 57 Irrigate 13,14,15,16 (7,8 Composition 1 daily, No Urine)
Day 58 Irrigate 13,14,15,16 (7,8 Composition 1 daily, No Urine)
Day 59 Irrigate 13,14,15,16 (7,8 Composition 1 daily, No Urine)
Day 60 Irrigate 13,14,15,16 (7,8 Composition 1 daily, No Urine
Day 61 Irrigate, Foliar, 13,14,15,16
Day 62 Irrigate 13,14,15,16 (7,8 Composition 1 daily, No Urine)
Day 63 Irrigate 13,14,15,16 (7,8 Composition 1 daily, No Urine)
Day 64 Irrigate 13,14,15,16 (7,8 Composition 1 daily, No Urine)
Day 65 Irrigate 13,14,15,16
Day 66 Irrigate, Foliar, 13,14,15,16
Day 69 Irrigate 13,14,15,16 (7,8 Composition 1 daily, No Urine)
Day 70 Irrigate 13,14,15,16 (Control, 7, 8 complete recovery)
Day,71 Irrigate, 13, 14, 15, 16
Day 76 Irrigate, Foliar, 13,14,15,16
Day 76 Irrigate, 13, 14, 15, 16
Day 77 Irrigate, 13, 14, 15, 16

TABLE 2

Plot Map

| | |
|---|---|
| 1. Control (No Application) | 2. Urine Daily |
| 3. Urine Daily Composition 1 Daily | 4. Composition 2 Daily Urine Daily |
| 5. Urine Daily Composition 2 Daily Composition 1 Daily | 6. Urine Daily Composition 1 Weekly |
| 7. Urine Daily Composition 2 Weekly | 8. Urine Daily Composition 2 Weekly Composition 1 Weekly |
| 9. Urine Daily 50/50 Composition 2/ Composition 1 Solution Daily | 10. Urine Daily Composition 2 Daily Composition 1 Daily |
| 11. Male 4oz Urine Daily | 12. Female 4oz Urine Daily |
| 13. Male 1/2 U Daily Composition 1 Weekly | 14. Female 1/2 U Daily Composition 1 Weekly |
| 15. Male 1/4 U Daily Composition 1 Weekly | 16. Female 1/4 U Daily Composition 1 Weekly |

Based on the forgoing, compositions 1 and 2 showed the most improvement when applied with urine. Compositions 1 and 2 also recovered after urine application was stopped and fertilizer applications continued. Composition 1 only also showed improvement when applied weekly after urine and recovered within two weeks after urine application stopped. Compositions 1 and 2 together are most effective when applied daily or weekly in areas stressed by daily canine urine, after the stress by urine has stopped. Composition 1 is most effective when applied weekly. Composition 1 and/or composition 2 are least effective when applied daily.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the invention, and are not restrictive of the invention, as claimed.

The invention claimed is:

1. A liquid formulation for reducing or rectifying plant damage from a canine urine deposition consisting essentially of:
choline ranging from between 1% to 5% by weight of said formulation as an active agent wherein choline is in the form of choline bitartrate,
an emulsifier ranging from 1% to 10% of said liquid formulation,
humic and/or fulvic acid,
water and
an element selected from the group consisting of: nitrogen, phosphorus, potassium, calcium, magnesium, silicon, sulfur, iron and zinc,
wherein said liquid formulation upon application to turf has the physical property of reducing or rectifying plant damage from a canine urine deposition.

2. The liquid formulation of claim 1 further consisting essentially of an active ingredient selected from the group consisting of:
hormones, vitamins, amino acids, enzymes, organic acids, sugars, catalysts, and antioxidants.

3. The liquid formulation of claim 1 further consisting essentially of: a non-active ingredient selected from the group consisting of: wetting agents and fillers.

4. The liquid formulation of claim 1 wherein said humic or fulvic acids do not exceed 0.5% by weight of the formulation.

5. The liquid formulation of claim 2 wherein said sugars range from between 5% and 10% by weight of said formulation.

6. A product made by the process of admixing:
a fertilizer with the composition of claim 1.

7. The liquid formulation of claim 2 wherein one of the vitamins is vitamin K.

8. The liquid formulation of claim 2 wherein one of the vitamins is a vitamin B-12.

9. The liquid formulation of claim 2 wherein one of the vitamins is folic acid.

10. The liquid formulation of claim 1 wherein the emulsifier is monoethanolamine.

11. The liquid formulation of claim 1 further consisting essentially of a sugar.

12. The liquid formulation of claim 1 further consisting essentially of a trimethylglycine.

13. A liquid formulation for reducing or rectifying plant damage from a canine urine deposition consisting essentially of:
choline ranging from between 1% to 5% by weight of said formulation as an active agent, wherein choline is in the form of choline bitartrate;
an emulsifier ranging from 1% to 10% of said liquid formulation;
an organic acids, wherein one of said organic acids is selected from the group consisting of: humic and fulvic acid;
trimethylglycine;
and
water,
wherein said liquid formulation upon application to turf has the physical property of reducing or rectifying plant damage from a canine urine deposition.

14. The liquid formulation of claim 13 further consisting essentially of a vitamin and wherein said vitamin is selected form the group consisting of: vitamin K, vitamin B-12 and folic acid, or a combination thereof.

15. The liquid formulation of claim 13 further consisting essentially of an active ingredient selected from the group consisting of: hormones, amino acids, enzymes, organic acids, sugars, catalysts, and antioxidants.

16. The liquid formulation of claim 13 wherein said humic or fulvic acids do not exceed 0.5% by weight of the formulation.

* * * * *